(12) United States Patent
Kim et al.

(10) Patent No.: US 11,738,063 B2
(45) Date of Patent: *Aug. 29, 2023

(54) **PHARMACEUTICAL COMPOSITION FOR PREVENTING OR TREATING NEURODEGENERATIVE DISEASES WHICH INCLUDES FLOWER EXTRACT OF *DAPHNE GENKWA* OR FRACTIONS THEREOF AS ACTIVE INGREDIENT**

(71) Applicant: KOREA RESEARCH INSTITUTE OF BIOSCIENCE AND BIOTECHNOLOGY, Daejeon (KR)

(72) Inventors: Won Gon Kim, Daejeon (KR); Baek Soo Han, Daejeon (KR); Jeong Su Byun, Daejeon (KR); Ha Young Choi, Daejeon (KR)

(73) Assignee: KOREA RESEARCH INSTITUTE OF BIOSCIENCE AND BIOTECHNOLOGY, Daejeon (KR)

(*) Notice: Subject to any disclaimer, the term of this patent is extended or adjusted under 35 U.S.C. 154(b) by 180 days.

This patent is subject to a terminal disclaimer.

(21) Appl. No.: 17/012,238

(22) Filed: Sep. 4, 2020

(65) Prior Publication Data

US 2021/0106645 A1 Apr. 15, 2021

Related U.S. Application Data

(62) Division of application No. 16/349,762, filed as application No. PCT/KR2017/012790 on Nov. 13, 2017, now Pat. No. 10,792,323.

(30) Foreign Application Priority Data

Nov. 14, 2016 (KR) .......................... 10-2016-0150983

(51) Int. Cl.
*A61K 36/83* (2006.01)
*A61P 25/16* (2006.01)

(52) U.S. Cl.
CPC .............. *A61K 36/83* (2013.01); *A61P 25/16* (2018.01)

(58) Field of Classification Search
None
See application file for complete search history.

(56) References Cited

FOREIGN PATENT DOCUMENTS

| CN | 105348095 A | | 2/2016 |
|----|-------------|---|--------|
| CN | 105520928 A | | 4/2016 |
| KR | 1020130057878 | * | 6/2013 |

OTHER PUBLICATIONS

Chen et al., "Toxicity of daphnane-type diterpenoids from Genkwa Flos and their pharmacokinetic profile in rat", Phytomedicine, 2013, vol. 21, No. 1, pp. 82-89.
Han, "Research on Chemical Composition and Quality Standards of Finished Flowers", Han Wei, China Excellent Master's Degree Thesis Full-text Database—Series of Medicine and Health Science and Technology, No. 5, E057-64, 2011.
Han et al., "Daphnane Diterpenes from Daphne genkwa Activate Nurr1 and Have a Neuroprotective Effect in an Animal Model of Parkinson's Disease", Journal of Natural Products, 2016, 79(6): 1604-1609.
Li et al., "Daphnane-Type Diterpenoids from the Flower Buds of Daphne genkwa", Helvetica Chimica Acta, 2010, 93 (6): 1172-1179.
Zhan et al., "Novel diterpenoids with potent inhibitory activity against endothelium cell HMEC and cytotoxic activities from a well-known TCM plant Daphne genkwa", Bioorganic & Medicinal Chemistry, 2005, 13(3): 645-655.

* cited by examiner

*Primary Examiner* — Michael V Meller
(74) *Attorney, Agent, or Firm* — Vorys, Sater, Seymour and Pease LLP; Mih Suhn Koh (57) ABSTRACT

The present invention relates to a pharmaceutical composition and health functional food for preventing or treating neurodegenerative diseases which include a flower extract of *Daphne genkwa* or fractions thereof as an active ingredient. The pharmaceutical composition and health functional food for preventing or treating neurodegenerative diseases are, not like extracts from stems and/or roots of *Daphne genkwa*, free from genotoxicity and have superior prophylactic or treatment effects against neurodegenerative diseases.

6 Claims, 7 Drawing Sheets

[Fig. 1A] extract of stalk and root of Daphene genkwa

[Fig. 1B] extract of flower of Daphne genkwa

extract of flower of Daphne genkwa

PHARMACEUTICAL COMPOSITION FOR PREVENTING OR TREATING NEURODEGENERATIVE DISEASES WHICH INCLUDES FLOWER EXTRACT OF *DAPHNE GENKWA* OR FRACTIONS THEREOF AS ACTIVE INGREDIENT

BACKGROUND

Technical Field

The present invention relates to pharmaceutical composition for preventing or treating neurodegenerative disease comprising an extract of flower of *Daphne genkwa* or a fractions thereof as active ingredient

Background Art

Neurodegenerative diseases are associated with symptoms in which neurons degenerate, lose their function, and often die. Patients with neurodegenerative disease may undergo severe deterioration in cognitive or motor ability. Because these diseases are generally progressive, therefore, the quality of life and life expectancy of the patients may be considerably reduced.

These diseases include Parkinson's disease (PD), Alzheimer's disease (AD), amyotrophic lateral sclerosis (ALS), Huntington's disease (HD), fronto-temporal dementia, cortico basal degeneration, progressive supranuclear palsy (PSP), and other diseases.

Meanwhile, it is known that Nurr1 (nuclear receptor-related 1) protein is implicated in a considerable number of neurodegenerative diseases. The term "Nurr1" refers to nuclear receptor-related 1 protein, also known as NR4A2 (nuclear receptor subfamily 4, group A, member 2), which is known to be encoded by the human NR4A2 gene. Although the Nurr1 protein is an orphan nuclear receptor whose ligand has not yet been clearly identified, it was identified that the Nurr1 protein plays a key role in maintaining the dopaminergic system in the brain. It is known that, when aberrations in the Nurr1 or NR4A2 gene occur, the function of the dopaminergic system is damaged to cause Parkinson's disease and a wide range of inflammatory and neuropathic diseases, including rheumatoid arthritis, schizophrenia and manic depression. Parkinson's disease is a typical neurodegenerative disease that is caused by Nurr1 dysfunction.

Parkinson's disease is one of the major diseases in modern aging society, which is characterized by tremor, stiffness, bradykinesia, and gait abnormality, and is a chronic disease caused by a lack of neurotransmitters called dopamine in the substantia nigra and corpus striatum of the brain.

Known drugs for treating Parkinson's disease include L-dopa drugs, dopamine receptor agonists, anti-cholinergic drugs, Eldepryl, etc. Most of these drugs do not provide causal treatment of Parkinson's disease, but act to control conditions, and thus need to be administered continually. Although many medicines have been produced and commercialized for the treatment of Parkinson's disease so far, an essential therapeutic agent for completely treating Parkinson's disease has not yet been developed.

Recently, it has been reported that compounds that activate the function of Nurr1, which plays an important role in the differentiation, growth and maintenance of dopaminergic neurons, have medicinal effects on Parkinson's disease and can be applied as a disease target of a therapeutic agent for Parkinson's disease.

In the Korean Patent Registration No. 10-1631589 filed by the present applicant, it has been confirmed that the extract of stalk and/or root of *Daphne genkwa* is involved in the activation of Nurr1 and the symptoms of Parkinson's disease are alleviated when administered to an animal model of Parkinson's disease.

However, it has been confirmed that the extract of stalk and/or root of *Daphne genkwa* proposed by the present applicant were genotoxic in the bacterial reverse mutation assay and the chromosome aberration assay during the non-clinical stability testing for the development of natural product new drug.

In order to solve such problems, the inventors of the present invention have found that flower of *Daphne genkwa* which is a well-known traditional oriental medicine is more effective for prevention or treatment of neurodegenerative diseases without genetic toxicity, thus completing the present invention.

PRIOR ART

Patent

Korean Patent Registration No. 10-1631589

DETAILED DESCRIPTION OF THE INVENTION

Technical Problem

The object of present invention is to provide pharmaceutical composition for preventing or treating neurodegenerative disease comprising the extract of flower of *Daphne genkwa* or a fractions thereof as active ingredient.

Also, the present invention is to provide a health functional food for preventing or ameliorating neurodegenerative disease comprising the extract of flower of *Daphne genkwa* or a fractions thereof.

Technical Solution

Hereinafter, the present invention will be described in detail.

In one aspect of the present invention, the present invention provides a pharmaceutical composition for preventing or treating neurodegenerative diseases comprising an extract of flower of *Daphne genkwa* or a fraction thereof as an active ingredient.

As used herein, the term "*Daphne genkwa*" refers to a deciduous shrub of dicotyledonous Myrtales thymelaeaceae, and is also called lilac daphne.

It grows mainly on the seashore. In Chinese medicine, it is used to treat symptoms such as diuresis, hydrops and nephritis. Dried-buds of *Daphne genkwa* are called "flower" or "uan flower" and are used as medicinal materials and are known to have some toxicity. It is known that the extract of flower of *Daphne genkwa* contains genkwanin, hydroxygenkwanin, apigenin and sitosterol, as well as benzoic acid and irritating essential oil substance.

As used herein, the term "extract of flower of *Daphne genkwa*" refers to an extract obtained from the flower or bud of *Daphne genkwa*, preferably an extract obtained by extracting the flower or bud of *Daphne genkwa* with water or organic solvent, and specifically an extract obtained by extracting the flower or bud of *Daphne genkwa* with water, $C_1$-$C_4$ lower alkyl alcohol or a mixed solvent thereof.

The extract of flower of *Daphne genkwa* according to an embodiment of the present invention is preferably an extract obtained by extracting with 80% ethanol.

According to one embodiment of the present invention, the extract of flower of *Daphne genkwa* is obtained using water, an organic solvent such as $C_1$-$C_4$ lower alkyl alcohol such as methanol, ethanol, butanol or the like, or an $C_1$-$C_4$ lower alkyl alcohol aqueous solution to the flower or bud of *Daphne genkwa*. The extract of flower of *Daphne genkwa* may include Genkwanin N or Yuanhuacin compounds.

The Genkwanin N can be produced by a method known to those skilled in the art as a terpenoid represented by Formula 1, specifically, a diterpene ester compound, and preferably can be extracted and separated from the flower or bud of *Daphne genkwa*.

[Formula 1]

The Yuanhuacin can be produced by a method known to those skilled in the art as a terpenoid represented by Formula 2, specifically, a diterpene ester compound, and preferably can be extracted and separated from the flower or bud of *Daphne genkwa*.

[Formula 2]

The term "fraction" used in the present invention means an active fraction obtained by fractionating a substance having an activity of interest in the present invention from the extract of flower of *Daphne genkwa* using a specific solvent.

In another example of the present invention, the extract of flower of *Daphne genkwa* is obtained by separating a fraction layer of each solvent using a mixed solvent of an organic solvent such as hexane, ethyl acetate, butanol, or distilled water, and the like, and the active ingredient can be isolated and purified in high purity using a separation method known in the art such as chromatography to produce fractions. Fractions obtained through various purification methods are also included in the fractions of the present invention. The fractions of the extract of flower of *Daphne genkwa* may include Genkwanin N or Yuanhuacin compounds.

Figure 1A:
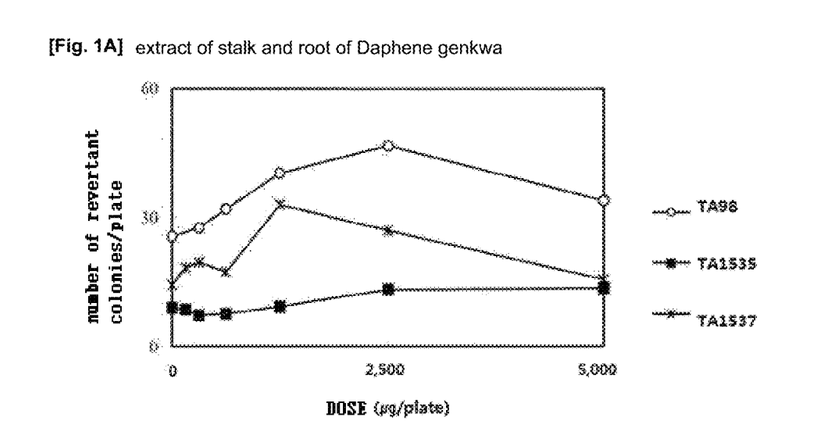
FIG. 1A shows the induction of a reverse mutation of the extract of stalk and/or root of *Daphne genkwa*.
Figure 1B:
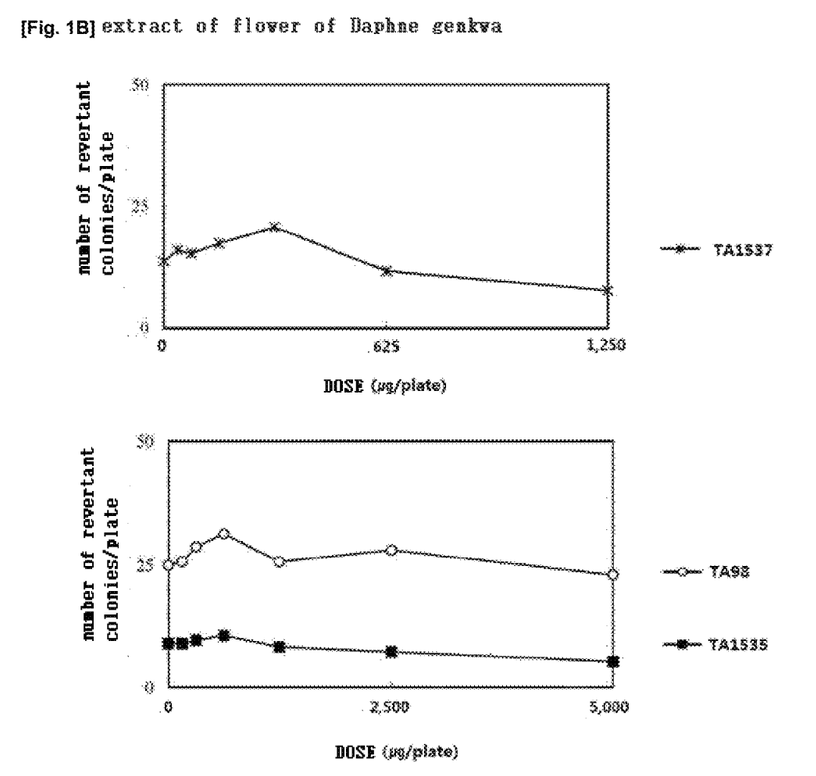

The extract of flower of *Daphne genkwa* or the fractions thereof of the present invention may include not only the extract obtained by the above-mentioned extraction solvent but also the extract obtained through ordinary purification process. The inventors of the present invention confirmed that genotoxicity was observed in a bacterial reverse mutation assay and a chromosome aberration assay in the non-clinical stability trial for development of natural products as new drugs, in the case of the extract derived from the stem and root of *Daphne genkwa* of Korean Patent Registration No. 10-1631589 filed by the present applicant (FIG. 1A.). Otherwise, genetic toxicity of the extract of flower of *Daphne genkwa* was examined, and it was confirmed that neither the bacterial reverse mutation assay nor the chromosome aberration assay showed genotoxicity (FIG. 1B).

Figure 2A:
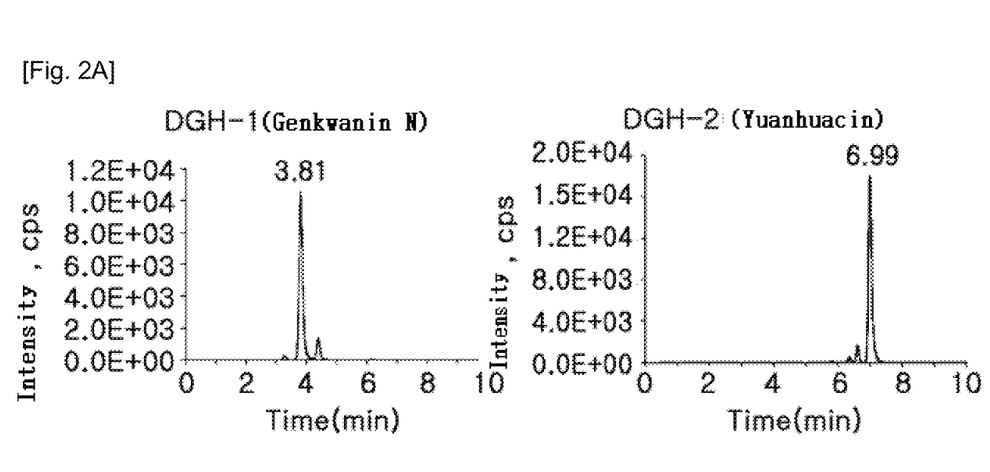
FIGS. 2A and 2B show the results of analysis of the active ingredient of the extract of flower of *Daphne genkwa* by LC-MS/MS method.
Figure 2B:
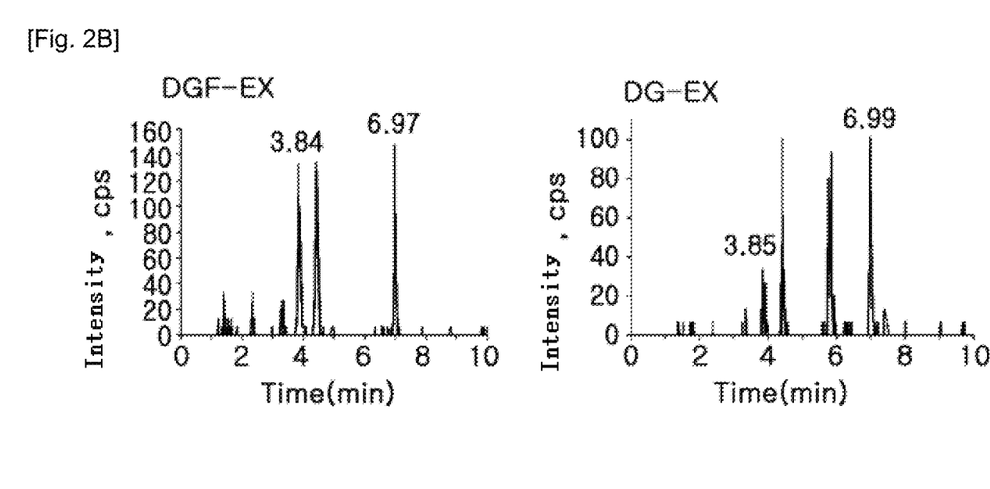

The present inventors also compared and analyzed the active ingredients of the extract of flower of *Daphne genkwa* and of the extract derived from the stem and root of *Daphne genkwa*, and found that both Genkwanin N and Yuanhuacin were detected as active ingredients in both the extract of flower of *Daphne genkwa* and the extract derived from the stem and root of *Daphne genkwa*. As a result of quantifying each active ingredient, it was confirmed that the amounts of Genkwanin N and Yuanhuacin of the extract of flower of *Daphne genkwa* were about 7.32 times and 1.23 times greater than those derived from the stem and root of *Daphne genkwa*, respectively (FIG. 2).

Figure 4:
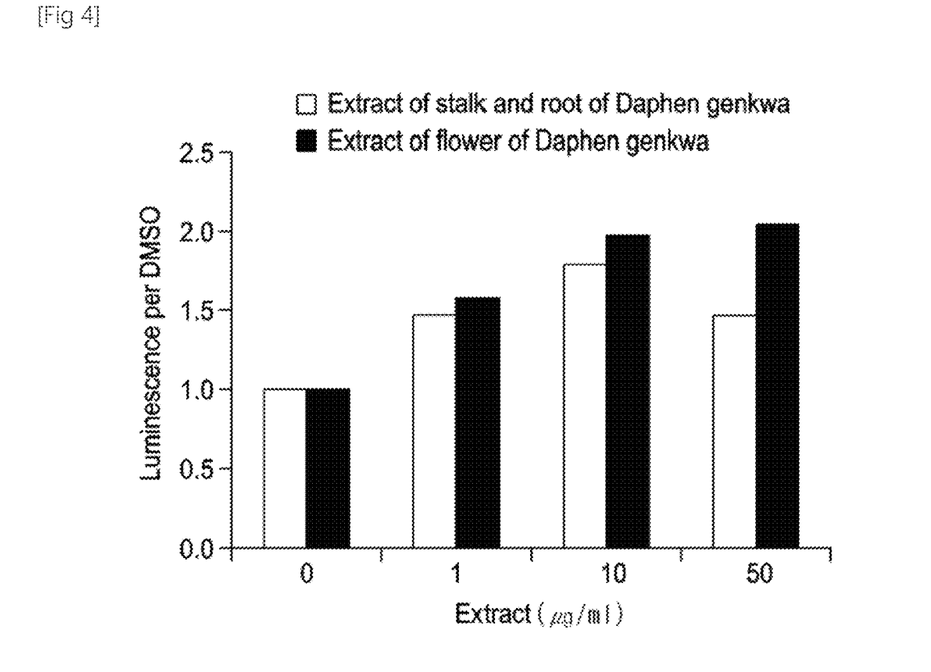
FIG. 4 is a graph showing the results of comparative experiments showing the change of Nurr1 activity according to each concentration of extract of stalk and/or root of *Daphne genkwa* and of extract of flower of *Daphne genkwa* through luciferase assay. DG-EX refers to the extract of stalk and/or root of *Daphne genkwa*, and DGF-EX refers to the extract of flower of *Daphne genkwa*.

Moreover, as a result of comparing the activity of the Nurr1 from the extract of flower of *Daphne genkwa* and the extract derived from the stem and root of *Daphne genkwa*, it was confirmed that the extract of flower of *Daphne genkwa* of the present invention showed higher activity than the extract derived from the stem and root of *Daphne genkwa* (FIG. 4).

Figure 5:
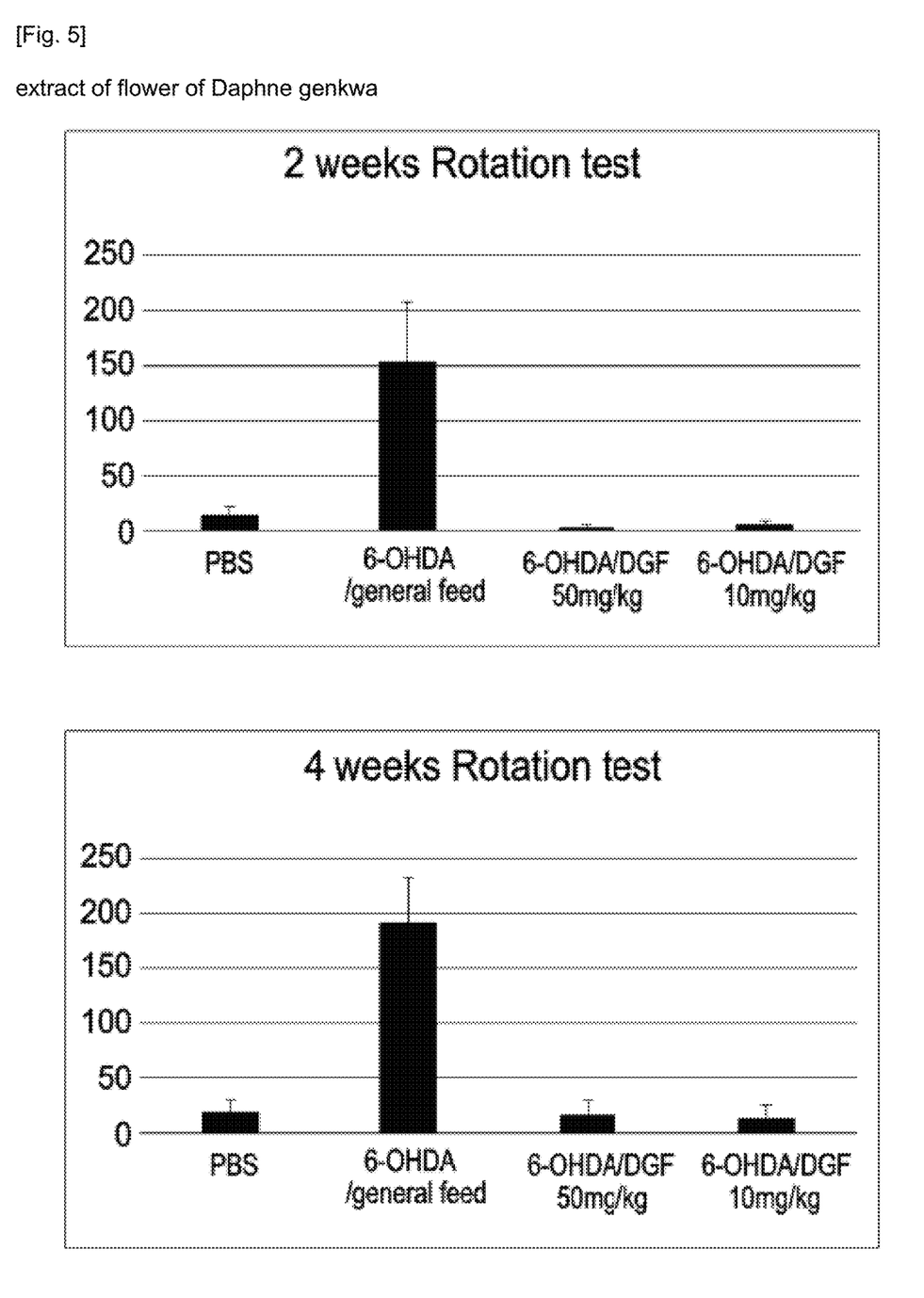
FIG. 5 is a graph showing the results of a rotation test after two or 4 weeks of feeding of the extract of flower of *Daphne genkwa* from 6-OHDA (6-hydroxydopamine) induced animal model of Parkinson's disease.

Furthermore, the present inventors have also carried out the apomorphine-induced rotation test after feeding a mixture containing the extract of flower of *Daphne genkwa* to a 6-OHDA-induced animal model of Parkinson's disease. As a result, it was confirmed that the number of rotation was significantly reduced when compared with the vehicle-treated group (control group) (FIG. 5).

Thus, the present inventors have found that the extract of flower of *Daphne genkwa* increases the activity of Nurr1 and is effective for preventing or treating various diseases caused by the damage of dopaminergic neurons directly affected by the activity of Nurr1, for example, various neurodegenerative diseases caused by dysfunction of Nurr1 other than Parkinson's disease and Parkinson's disease.

Therefore, the pharmaceutical composition comprising the extract of flower of *Daphne genkwa* of the present invention or fractions thereof as an active ingredient has an effect on the activation of the Nurr1, so that it is effective for preventing or treating various diseases caused by the damage of dopaminergic neurons directly affected by the activity of Nurr1, for example, various neurodegenerative diseases caused by dysfunction of Nurr1 other than Parkinson's disease and Parkinson's disease.

As used herein, the term "neurodegenerative diseases" refers to diseases associated with conditions in which neurons degenerate, lose their function, and often die. The neurodegenerative diseases include, but are not limited to, Parkinson's disease (PD), Alzheimer's disease (AD), amyotrophic lateral sclerosis (ALS), Huntington's disease (HD), frontotemporal dementia, cortico basal degeneration, and progressive supranuclear palsy (PSP). Preferably, the neurodegenerative disease according to the present invention is Parkinson's disease.

The pharmaceutical composition of the present invention may include a pharmaceutically acceptable carrier, excipient or diluent in addition to the active ingredient or its fractions described above. Examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, Polyvinylpyrrolidone, water, methylhydroxybenzoate, propylhydroxybenzoate, talc, magnesium stearate and mineral oil.

The pharmaceutical composition of the present invention may be formulated in the oral dosage form of powders, granules, tablets, capsules, suspensions, emulsions, syrups, aerosols, etc. or in the form of an external preparation, a suppository or a sterile injection solution according to conventional methods. In detail, when formulating, it can be prepared by using diluents or excipients such as fillers, weighing agents, binders, humectants, disintegrants, surfactants and the like which are generally used. Solid formulations for oral administration include, but are not limited to, tablets, pills, powders, granules, capsules, and the like. Such a solid preparation may be prepared by mixing at least one excipient such as starch, calcium carbonate, sucrose, lactose, gelatin and the like. In addition to simple excipients, lubricants such as magnesium stearate and talc may also be used. Liquid formulations for oral administration, liquid paraffin, and various excipients such as wetting agents, sweeteners, fragrances, preservatives and the like may be also used. Formulations for parenteral administration include sterile aqueous solutions, non-aqueous solvents, suspensions, emulsions, lyophilized preparations and suppositories. Non-aqueous solvents and suspensions may include propylene glycol, polyethylene glycol, vegetable oils such as olive oil, injectable esters such as ethyl oleate, and the like. Examples of suppositories include withexol, macrogol, tween 61, cacao butter, laurin, and glycerogelatin.

The pharmaceutical composition of the present invention can be administered orally or parenterally (for example, intravenously, subcutaneously, intraperitoneally or topically) according to the intended method.

The pharmaceutical composition according to the present invention may be administered in a pharmaceutically effective amount, that is, in an amount sufficient to prevent or treat the disease at a reasonable benefit/risk ratio applicable to medical prevention or treatment. The effective dosage level of the composition may be determined depending on the severity of the disease, the activity of the drug, the patient's age, weight, physical condition and sex, the patient's sensitivity to the drug, the time of administration of the inventive composition used, the route of administration of the composition, the excretion rate, the duration of treatment, factors including drugs used in combination with or contemporaneously with the composition of the present invention employed, and other factors well known in the medical arts, but may be suitably selected by those skilled in the art.

The dose or the dosage of the pharmaceutical composition comprising the extract of flower of *Daphne genkwa* or the fraction thereof according to the present invention as an active ingredient may vary depending on the patient's age, physical condition, body weight, etc., but, in general, it is preferable to administer it within the range of 0.01 to 1,000 mg/kg (weight)/day. And, it can be applied once a day or several times a day within a range of effective doses per day.

As another embodiment for achieving the above object, the present invention provides a health functional food for preventing or ameliorating a neurodegenerative disease comprising an extract of flower of *Daphne genkwa* or a fraction thereof.

The term "health functional food" used in the present invention means a food prepared and processed using raw materials or ingredients having useful functions in the human body in accordance with Law No. 6727 on Health Functional Foods, and "functional" means that the structure and function of the human body is ingested for the purpose of obtaining nutritional control or physiological effects and other useful effects for health use.

When the extract of flower of *Daphne genkwa* or a fraction thereof of the present invention is used as a food additive, the above extract or the fraction thereof may be added to the food or beverage as it is or in combination with other food additives. When the extract of flower of *Daphne genkwa* or the fraction thereof of the present invention is added during the production of food or beverage, the addition amount thereof is not particularly limited, but may be added in an amount of 1-5% by weight, preferably 1-3% by weight, based on the weight of the final food. However, in the case of long-term intake for the purpose of health and hygiene or for the purpose of controlling health, the addition amount may be less than the above range, but in the case where there is no problem in terms of safety, it may be used in an amount exceeding the above range.

The type of the food or beverage is not particularly limited, but includes all foods or beverages in a conventional sense, preferably meat, sausage, bread, chocolate, candy, snack, confectionery, pizza, ramen, noodles, gums, dairy products including ice cream, various soups, beverages, tea, drinks, alcoholic beverages and vitamin complexes.

When the extract of flower of *Daphne genkwa* or a fraction thereof of the present invention is added to a food, it is preferable to add together with an auxiliary component such as various nutrients, vitamins, electrolytes, flavors, colorants, pectic acid and its salts, alginic acid and its salts, organic acids, protective colloid thickeners, pH adjusting agents, stabilizers, preservatives, glycerin, alcohols and the like.

When the extract of flower of *Daphne genkwa* or the fraction thereof of the present invention is added to beverages, various sweeteners or natural carbohydrates may be added as an additional ingredient such as ordinary beverages. At this time, the sweetener is not particularly limited, but may be a natural sweetener such as tau marin or stevia extract or a synthetic sweetener such as saccharin or aspartame. Examples of the natural carbohydrate include, but are not limited to, monosaccharides (for example, glucose and fructose), disaccharides (for example, maltose and sucrose), polysaccharides (for example, dextrin and cyclodextrin), or sugar alcohols (for example, xylitol, sorbitol, erythritol, etc.) may be used.

The safety of the extract of flower of *Daphne genkwa* or its fractions of the present invention has been confirmed, and a health functional food comprising the same can prevent or ameliorate the symptoms of neurodegenerative diseases.

In another aspect of the present invention, the present invention provides a method for preventing or treating a neurodegenerative disease, comprising the step of administering a pharmaceutical composition comprising the extract of flower of *Daphne genkwa* or a fraction thereof as an active ingredient to a subject in need thereof.

The terms used in the present invention are the same as those described above, such as '*Daphne genkwa*', 'the extract of flower of *Daphne genkwa*', 'fraction', 'neurodegenerative diseases', and 'administration'.

In the present invention, the subject refers to an animal, and is typically a mammal capable of exhibiting beneficial effects in the treatment with the extract of the present invention. Preferred examples of such a subject include primates such as humans. Such subjects also include subjects with neurodegenerative disease symptoms or at risk of having such symptoms.

As another embodiment for achieving the above object, the present invention provides the use of the extract of flower of *Daphne genkwa* or a fraction thereof for preventing or treating of neurodegenerative diseases.

As another embodiment for achieving the above object, the present invention provides the use of the extract of flower of *Daphne genkwa* or a fraction thereof for producing a medicament having an effect of preventing or treating a neurodegenerative disease.

The terms used in the present invention are the same as those described above, such as '*Daphne genkwa*', 'the extract of flower of *Daphne genkwa*', 'fraction', 'neurodegenerative diseases'.

Effects of the Invention

The pharmaceutical composition comprising the extract of flower of *Daphne genkwa* or a fraction thereof of the present invention as an active ingredient exhibits an excellent effect of restoring the inhibition of the activity of Nurr1 by nerve injury without showing any side effects, and has an excellent effect in the prevention or treatment of neurodegenerative diseases caused by inhibition of the activity of Nurr1.

BRIEF DESCRIPTION OF THE DRAWINGS

FIG. 1B shows that the extract of flower of *Daphne genkwa* was not mutagenic. TA98 refers to the *Salmonella typhimurium* strain TA98, and TA1535 refers to the *Salmonella typhimurium* strain TA1535, and TA1537 refers to the *Salmonella typhimurium* strain TA1537.

FIG. 2A is the standard material DGH-1 (m/z 105.2>591.2) and DGH-2 (m/z 105.1>639.2), in FIG. 2B, DGF-EX is the extract of flower of *Daphne genkwa*, DG-EX is the extract of stalk and/or root of *Daphne genkwa*.

DETAILED DESCRIPTION

Hereinafter, the present invention will be described in more detail with reference to examples. However, these examples are for illustrative purposes only, and the scope of the present invention is not limited to these examples.

Comparative Example 1

Genotoxicity Test of the Extract of Stalk and/or Root of *Daphne genkwa*

In order to confirm in vitro genotoxicity of the extract of stalk and/or root of *Daphne genkwa* according to Korean Patent Registration No. 10-1631589 filed by the present applicant, a bacterial reverse mutation assay and a chromosomal aberration test were performed as described below.

1-1. Production of the Extract of Stalk and/or Root of *Daphne genkwa*

14 kg of stem of *Daphne genkwa* and 6 kg of root of *Daphne genkwa* were finely cut and immersed in 120 L of 80% ethanol for 48 hours, and filtered to separate it into a solid component and a first liquid component. The separated solid component were again immersed in 120 L 80% ethanol for 24 hours, and filtered to obtain a second liquid component. The obtained first liquid component and the second liquid component were mixed with each other, and the mixture was concentrated under reduced pressure. The residue was freeze-dried, thereby obtaining 1140.9 g of the extract of stalk and/or root of *Daphne genkwa* (hereinafter referred to as "DG-EX").

1-2 Bacterial Reverse Mutation Assay

In order to confirm genotoxicity of the extract of stalk and/or root of *Daphne genkwa*, a bacterial reverse mutation assay was conducted on the basis of the guidelines of Ministry of Food and Drug Safety by Biotoxtech, a GLP (Good Laboratory Practice) organization.

In order to confirm the genomic mutation induction of DG-EX obtained in the Test 1-1, a bacterial reverse mutation assay for the presence of metabolic activation system (S9+) and non-existence (S9−) was performed with *Salmonella typhimurium* TA98, TA100, TA1535, TA1537, histidine requiring strain, and *Escherichia coli* WP2uvrA (pKM101), a tryptophan requiring strain.

(1) Capacity Setting Test

In order to set the maximum dose of the bacterial reverse mutation assay of present test, the recommended dose of 5,000 μg/plate was used as the maximum capacity, and the capacity setting test was carried out at 1,250, 313, 78.1, and 19.5 μg/plate in common rate 4.

As a result, it was found that inhibition of growth by DG-EX was observed on 5,000 μg/plate of TA98 strain, and above 313 μg/plate of TA100, TA1535 and TA1537 strains in the absence of the metabolism activation system, and on 5,000 μg/plate of TA100, TA1535 and TA1537 strains in the presence of metabolic activation system.

Growth inhibition was not observed in TA98 and WP2uvrA (pKM101) strains in the presence of metabolic activation system, and in WP2uvrA (pKM101) strain in the absence of metabolic activation system.

Therefore, the capacity of the bacterial reverse mutation assay as the present test was set as shown in Table 1 below. In addition, a negative control and a positive control were set.

TABLE 1

| strain | S9 mix | DOS (μg/plate) |
|---|---|---|
| TA98 | − | 5,000, 2,500, 1,250, 625, 313, 156 |
|  | + | 5,000, 2,500, 1,250, 625, 313 |
| TA100, TA1535, TA1537 | − | 313, 156, 78.1, 39.1, 19.5, 9.77 |
|  | + | 5,000, 2,500, 1,250, 625, 313, 156 |
| WP2uvrA(pKM101) | −/+ | 5,000, 2,500, 1,250, 625, 313 |

Precipitation of the test substance DG-EX was not observed at all doses in the presence and absence of metabolic activation system.

(2) Bacterial Reverse Mutation Assay

Each strain was treated with the test substance DG-EX at the above concentrations and cultured, and the number of bacterial reverse mutation colonies was visually counted. The results are shown in Table 2 below.

TABLE 2

| Strain | Test substance | Dose level (μg/plate) | Individual revertant colony counts | Mean | S.D. |
|---|---|---|---|---|---|
| TA98 | Dimethyl sulfoxide | 0 | 27, 26, 24 | 26 | 2 |
|  | DG-EX | 313 | 28, 25, 30 | 28 | 3 |
|  |  | 625 | 30, 31, 35 | 32 | 3 |
|  |  | 1,250 | 36, 43, 42 | 40 | 4 |
|  |  | 2,500 | 52, 45, 43 | 47 | 5 |
|  |  | 5,000 | 36, 30, 36 | 34 | 3 |
|  | 2-Aminoanthracene (2-AA) | 1.0 | 358, 366, 362 | 362 | 4 |
| TA100 | Dimethyl sulfoxide | 0 | 118, 117, 115 | 117 | 2 |
|  | DG-EX | 156 | 110, 117, 103 | 110 | 7 |
|  |  | 313 | 116, 116, 123 | 118 | 4 |
|  |  | 625 | 123, 127, 133 | 128 | 5 |
|  |  | 1,250 | 192, 181, 205 | 193 | 12 |
|  |  | 2,500 | 171, 176, 184 | 177 | 7 |
|  |  | 5,000 | 117*, 110*, 119* | 115 | 5 |
|  | 2-Aminoanthracene (2-AA) | 2.0 | 596, 608, 572 | 592 | 18 |
| TA1535 | Dimethyl sulfoxide | 0 | 9, 11, 7 | 9 | 2 |
|  | DG-EX | 156 | 7, 10, 9 | 9 | 2 |
|  |  | 313 | 6, 8, 8 | 7 | 1 |
|  |  | 625 | 9, 9, 5 | 8 | 2 |
|  |  | 1,250 | 10, 8, 10 | 9 | 1 |
|  |  | 2,500 | 12, 15, 13 | 13 | 2 |
|  |  | 5,000 | 15*, 15*, 11* | 14 | 2 |
|  | 2-Aminoanthracene (2-AA) | 3.0 | 98, 112, 94 | 101 | 9 |
| TA1537 | Dimethyl sulfoxide | 0 | 14, 13, 16 | 14 | 2 |
|  | DG-EX | 156 | 20, 18, 17 | 18 | 2 |
|  |  | 313 | 20, 18, 21 | 20 | 2 |
|  |  | 625 | 16, 17, 19 | 17 | 2 |
|  |  | 1,250 | 32, 30, 37 | 33 | 4 |
|  |  | 2,500 | 25*, 27*, 29* | 27 | 2 |
|  |  | 5,000 | 14*, 16*, 17* | 16 | 2 |
|  | 2-Aminoanthracene (2-AA) | 3.0 | 128, 136, 122 | 129 | 7 |
| WP2uvrA (pKM101) | Dimethyl sulfoxide | 0 | 163, 150, 151 | 155 | 7 |
|  | DG-EX | 313 | 170, 152, 169 | 164 | 10 |
|  |  | 625 | 170, 176, 166 | 171 | 5 |
|  |  | 1,250 | 180, 163, 162 | 168 | 10 |
|  |  | 2,500 | 176, 159, 169 | 168 | 9 |
|  |  | 5,000 | 168, 167, 153 | 163 | 8 |
|  | 2-Aminoanthracene (2-AA) | 2.0 | 445, 462, 480 | 462 | 18 |

S.D: Standard Deviation
*Indicates growth inhibition

As a result, at the 1,250 μg/plate of the TA1537 strain in the presence of the metabolic activation system, the number of reverse mutation colonies increased more than twice as much as that of the negative control, and above 2,500 μg/plate, growth inhibition by DG-EX was observed and the number of reverse mutation colonies tended to decrease.

In TA98, TA100, TA1535, TA1537 and WP2uvrA (pKM101) strains in the absence of metabolic activation system and TA98, TA100, TA1535 and WP2uvrA (pKM101) strains in the presence of metabolic activation system, regardless of the presence or absence of the metabolic activation system in the test substance group, the number of reverse mutation colonies did not exceed twice the negative control group and no dose-dependent increases were observed for all the strains of each strain. The number of reverse mutation colonies of the positive control for each strain The number of reverse mutation colonies of the positive control for each strain was more than twice as high as that of the negative control. The results are shown in FIG. 1.

As shown in FIG. 1A, under the present test conditions, the test substance DG-EX was found to be mutagenic by increasing the number of reverse mutation colonies in the TA1537 strain in the presence of the metabolic activation system more than twice that of the negative control.

1-3 Chromosome Aberration Assay

In order to confirm genotoxicity of extract of stalks and root of *Daphne genkwa*, a chromosome aberration assay was performed on the basis of the guidelines of Ministry of Food and Drug Safety in Biotoxtech, a GLP (Good Laboratory Practice) organization.

To confirm the structural aberration of the chromosome of DG-EX obtained in the Test substance 1-1, the presence of structural aberration of the chromosome was evaluated using CHL (Chinese Hamster Lung)/IU cells, a mammalian cell line.

(1) Cell Proliferation Inhibition Test

For the highest capacity setting of this test, the chromosome aberration assay, cell proliferation inhibition test was carried out with the highest dose of DG-EX 5,000 μg/mL at the following doses of 2,500, 1,250, 625, 313, 156, 78.1, 39.1, and 19.5 μg/ml. The relative population doubling (RPD) after DG-EX treatment was calculated and used as an indicator of cell proliferation inhibition.

As a result, cytotoxicity was observed in the presence or absence of the metabolic activation system and in the absence of the metabolic activation system of the continuous treatment method. The dose that specifically inhibited cell proliferation by more than 50% was more than 1,250 μg/mL in the presence and absence of the metabolic activation system of the short-term treatment method and more than 625 μg/mL in the absence of the metabolic activation system of the continuous treatment method.

Therefore, the capacity of this test was set as shown in Table 3 below. Also, a negative control and a positive control were set.

TABLE 3

| treatment | S9 mix | dose of the present test (μg/mL) |
|---|---|---|
| short-term treatment | − | 1,200, 600, 300, 150 |
|  | + | 900, 450, 225, 113 |
| continuous treatment | − | 600, 300, 150, 75.0 |

The precipitation of the test substance was observed at more than 2,500 μg/mL in the presence and absence of the metabolic activation system of the short-term treatment method and in the absence of the metabolic activation system of the continuous treatment method.

(2) Chromosome Aberration Assay

As a result of the chromosome aberration assay, the frequencies of cells with numerical aberration were significantly increased at 12.5% and 13.0% at 450 μg/mL and 900 μg/mL in the presence of the metabolic activation system of the short-term treatment method, which was statistically significantly increased when compared with the negative control (0%). The frequencies of cells with structural aberration were 6.0 and 8.0%, respectively, and statistically significant increase when compared with negative control (0%) (data not shown).

In the absence of the metabolism activity system of the short-term treatment method and in the absence of the metabolism activity system of the continuous treatment method, the frequency of chromosome aberration was less than 5%, and no chromosomal aberration was observed, and no statistical significance was observed when compared with the negative control group.

In the positive control group for each treatment group, the frequency of cells with aberrations was more than 10%, which was statistically higher than that in the negative control group.

Thus, in order to clarify the positive results of the structural aberration in the presence of the metabolic activation system of the short-term treatment method, confirmation tests were carried out in the same manner as in this test with the capacity of the following Table 4.

TABLE 4

| treatment | S9 mix | dose of confirmation test (μg/mL) |
|---|---|---|
| short-term treatment | + | 1,200, 1,100, 1,000, 900 |

As a result of the confirmation test, the frequency of cells with numerical aberration was confirmed to be 12.5, 11.5, 10.0 and 8.5% at 900, 1,000, 1,100 and 1,200 μg/mL in the presence of the metabolic activation system of the short-term treatment method, and was statistically significantly increased when compared with the negative control group. The frequencies of cells with structural aberrations were found to be 7.5, 7.0, 8.5 and 4.5%, which was statistically significantly increased when compared to the negative control group. The results are shown in Table 5 below.

TABLE 5

| Test substance | Dose (μg/mL) | RPD (%) | S9 mix | Trt-Rec Time (hr) | No. of cell analyzed | Number of cells with structural aberrations | | | | | | | | | | Number of cells with numerical aberrations | | | | |
|---|---|---|---|---|---|---|---|---|---|---|---|---|---|---|---|---|---|---|---|---|
| | | | | | | ctb | csb | cte | cse | frg | ctg | csg | gap | | total (%) | | | | total | |
| | | | | | | | | | | | | | gap− | gap+ | end | pol | (%) | Others[a] |
| Dimethyl sulfoxide | 0 | 100 | + | 6-18 | 100 | 1 | 0 | 0 | 0 | 0 | 0 | 0 | 1 (0.5) | 1 (0.5) | 0 | 0 | 0 (0.0) | 0 |
| | | | | | 100 | 0 | 0 | 0 | 0 | 0 | 0 | 0 | | | 0 | 0 | | |
| DG-EX | 900 | 66.5 | + | 6-18 | 100 | 1 | 0 | 6 | 0 | 0 | 0 | 0 | 15## (7.5) | 15 (7.5) | 0 | 12 | 25## (12.5) | 0 |
| | | | | | 100 | 2 | 0 | 5 | 1 | 0 | 0 | 0 | | | 0 | 13 | | |
| | 1,000 | 72.6 | + | 6-18 | 100 | 0 | 0 | 7 | 0 | 0 | 0 | 0 | 14## (7.0) | 15 (7.5) | 0 | 12 | 23## (11.5) | 0 |
| | | | | | 100 | 1 | 0 | 5 | 1 | 0 | 1 | 0 | | | 0 | 11 | | |

TABLE 5-continued

| Test substance | Dose (µg/mL) | RPD (%) | S9 mix | Trt-Rec Time (hr) | No. of cell analyzed | Number of cells with structural aberrations | | | | | | | | | Number of cells with numerical aberrations | | | Others[a] |
|---|---|---|---|---|---|---|---|---|---|---|---|---|---|---|---|---|---|---|
| | | | | | | ctb | csb | cte | cse | frg | ctg | csg | gap– total (%) gap– | gap+ | end | pol | total (%) | |
| | 1,100 | 60.0 | + | 6-18 | 100 | 2 | 0 | 7 | 0 | 0 | 2 | 0 | 17## (8.5) | 18 (9.0) | 0 | 10 | 20## (10.0) | 0 |
| | | | | | 100 | 3 | 0 | 6 | 0 | 0 | 0 | 0 | | | 0 | 10 | | |
| | 1,200 | 53.2 | + | 6-18 | 100 | 2 | 0 | 2 | 1 | 0 | 0 | 0 | 9# (4.5) | 9 (4.5) | 0 | 9 | 17## (8.5) | 0 |
| | | | | | 100 | 0 | 0 | 4 | 0 | 0 | 0 | 0 | | | 0 | 8 | | |
| B[a]P | 20 | 41.3 | + | 6-18 | 100 | 8 | 0 | 15 | 0 | 0 | 0 | 0 | 40* (20.0) | 40 (20.0) | 0 | 1 | 2 (1.0) | 0 |
| | | | | | 100 | 3 | 0 | 19 | 0 | 0 | 0 | 0 | | | 0 | 1 | | |

Abbreviation: ctg: chromatid gap, csg: chromosome gap, ctb: chromatid break, cte: chromatid exchange, csb: chromosome break, cse: chromosome exchange, frg: fragmentation, end: endoreduplication, pol: polyploidy, B[a]P: Benzo[a]pyrene, RPD: Relative Population Doubling, Trt-Rec time: Treatment-Recovery times,
gap–: total number of cells with structural aberration except gap,
gap+: total number of cells with structural aberration including gap
a): Excluded from the number of cells with chromosomal aberrations.
*: p<0.01, #: p<0.05, ##: p<0.01

Based on the above results, under the test conditions, the test substance DG-EX showed a frequency of cells having numerical aberration of 10% or more and a frequency of cells having a structural aberration of 5% or more and 10% or less in the presence of the metabolic activation system of the short-term treatment method, and was confirmed to have a chromosome aberration.

Example 1

Preparation of Extract of Flower of *Daphne genkwa*

3.5 kg of flower of *Daphne genkwa* was immersed in 70 L of 80% ethanol for 48 hours and filtered to separate a solid component and a first liquid component. The separated solid component were again immersed in 70 L of 80% ethanol for 24 hours and filtered to give a second liquid component. The obtained first liquid component and the second liquid component were mixed, the mixture was concentrated under reduced pressure. The residue was freeze-dried, thereby obtaining 859 g of extract of flower of *Daphne genkwa* (hereinafter referred to as "DGF-EX").

Example 2

Analysis of Active Ingredients of Extract of Flower of *Daphne genkwa*

The active ingredient of DGF-EX, an extract of flower of *Daphne genkwa* obtained in Example 1, was analyzed. For comparison, the active ingredient of DG-EX, the extract derived from the stem and root of *Daphne genkwa* obtained in Comparative Example 1-1, was also analyzed.

There are two active ingredients of DGH-1 and DGH-2 in the extract derived from the stem and root of *Daphne genkwa*. DGH-1 has very low UV extinction coefficient and it is very difficult to analyze DGH-1 in the extract by HPLC UV method.

Therefore, in order to effectively analyze both the active substances DGH-1 and DGH-2 in the extracts, they were analyzed by the multiple reaction monitoring (MRM) with LC-MS/MS. The MRM is a method of analyzing a specific substance in a complex sample by detecting a parent ion having a specific product ion.

As a result, the standards DGH-1 and DGH-2 were detected at 3.81 min and 6.99 min, respectively, and detected at $1.05 \times 10^4$ and $1.8 \times 10^4$ intensity at 0.1 ug injection, respectively, with similar sensitivities to the MRM method (FIG. 2).

Each extract was dissolved in MeOH at a concentration of 10 µg/mL and analyzed by MRM method with LC-MS/MS after 10 µl by HPLC. The active ingredients DGH-1 and DGH-2 were detected in both the extract of flower of *Daphne genkwa* (DGF-EX) and the extract derived from the stem and root of *Daphne genkwa* (DG-EX) (FIG. 2B).

Example 3

Chromosome Aberration Assay of the Extract of Flower of *Daphne genkwa*

In order to confirm in vitro genotoxicity of the extract of flower of *Daphne genkwa* obtained in Example 1, a bacterial reverse mutation assay and a chromosome aberration assay were performed as described below.
3-1 Bacterial Reverse Mutation Assay
In order to confirm genotoxicity of the extract of flower of *Daphne genkwa*, a bacterial reverse mutation assay was conducted on the basis of the guideline of Ministry of Food and Drug Safety in Biotoxtech, a GLP (Good Laboratory Practice) organization.

In order to confirm the genomic mutation induction of DGF-EX obtained in the Test 1, a bacterial reverse mutation assay in the presence of metabolic activation system (S9+) and non-existence (S9–) was performed with *Salmonella typhimurium* TA98, TA100, TA1535, TA1537, histidine requiring strain, and *Escherichia coli* WP2uvrA (pKM101), a tryptophan-requiring strain.
(1) Capacity Setting Test
In order to set the maximum dose of the bacterial reverse mutation assay of present test, the recommended dose of 5,000 µg/plate was used as the maximum capacity, and the capacity setting test was carried out at 1,250, 313, 78.1, and 19.5 µg/plate in common rate 4.

As a result, it was found that inhibition of growth by DGF-EX was observed above 1,250 µg/plate of TA98 and TA1535 strain, above 313 µg/plate of TA100 strain, above 78.1 µg/plate of TA1537 strain in the absence of the metabolism activation system, and on 5,000 µg/plate of TA98 and TA1535 strains, and above 1,250 µg/plate of TA100 and TA1537 strains in the presence of the metabolic activation system. Growth inhibition was not observed in strain WP2uvrA (pKM101) in the presence and absence of the metabolic activation system.

Therefore, the capacity of the bacterial reverse mutation assay as the present test was set as shown in Table 6 below. In addition, a negative control and a positive control were set.

TABLE 6

| STRAINS | S9 mix | dose of the present test (μg/plate) |
|---|---|---|
| TA98, TA1535 | – | 1,250, 625, 313, 156, 78.1, 39.1 |
|  | + | 5,000, 2,500, 1,250, 625, 313, 156 |
| TA100 | – | 313, 156, 78.1, 39.1, 19.5, 9.77 |
|  | + | 1,250, 625, 313, 156, 78.1, 39.1 |
| TA1537 | – | 78.1, 39.1, 19.5, 9.77, 4.88, 2.44 |
|  | + | 1,250, 625, 313, 156, 78.1, 39.1 |
| WP2uvrA(pKM101) | –/+ | 5,000, 2,500, 1,250, 625, 313 |

(2) Bacterial Reverse Mutation Assay

Each strain was treated with the test substance DGF-EX at the above concentrations and cultured, and the number of reverse mutation colonies was visually counted. The results are shown in Table 7 below.

As a result, the number of reverse mutation colonies did not exceed twice the negative control group, and no dose-dependent increase was observed for all capacities of each strain, regardless of the presence or absence of metabolic activation system in the test substance group. The number of positive mutant colonies for each strain was more than twice as high as that of the negative control. The results are shown in FIG. 1.

As shown in FIG. 1B, the test substance DGF-EX showed the number of reverse mutation colonies not more than 2 times that of the negative control for all doses in the stain TA98, TA1535, and TA1537 in the presence of the metabolic activity system, and showed no mutagenicity.

The inhibition of growth by test material was observed above 625 μg/plate of TA98 and TA1535 strain, above 156 μg/plate of TA100 strain, on 87.1 μg/plate of TA1537 strain in the absence of the metabolism activation system, and above 2,500 μg/plate of TA98 and TA1535 strains, and on 1,250 μg/plate of TA100 and above 625 μg/plate TA1537 strains in the presence of the metabolic activation system. Growth inhibition was not observed in strain WP2uvrA (pKM101) in the presence and absence of the metabolic activation system.

From the above results, under the test conditions, the test substance DGF-EX was judged not to be mutagenic.

TABLE 7

| Strain | Test substance | Dose level (μg/plate) | Individual revertant colony counts | Mean | S.D. |
|---|---|---|---|---|---|
| TA98 | Dimethylsulfoxide | 0 | 24, 24, 17 | 25 | 2 |
|  | DGF-EX | 156 | 25, 27, 25 | 26 | 1 |
|  |  | 313 | 35, 24, 27 | 29 | 6 |
|  |  | 625 | 35, 30, 29 | 31 | 3 |
|  |  | 1,250 | 29, 22, 26 | 26 | 4 |
|  |  | 2,500 | 35*, 22*, 27* | 28 | 7 |
|  |  | 5,000 | 22*, 25*, 22* | 23 | 2 |
|  | 2-Aminoanthracene (2-AA) | 1.0 | 436, 432, 452 | 440 | 11 |
| TA100 | Dimethylsulfoxide | 0 | 75, 87, 85 | 82 | 6 |
|  | DGF-EX | 39.1 | 80, 87, 91 | 86 | 6 |
|  |  | 78.1 | 73, 87, 92 | 84 | 10 |
|  |  | 156 | 72, 83, 95 | 83 | 12 |
|  |  | 313 | 91, 87, 79 | 86 | 6 |
|  |  | 625 | 81, 84, 83 | 83 | 2 |
|  |  | 1,250 | 73*, 67*, 81* | 74 | 7 |
|  | 2-Aminoanthracene (2-AA) | 2.0 | 811, 853, 849 | 838 | 23 |
| TA1535 | Dimethylsulfoxide | 0 | 9, 8, 10 | 9 | 1 |
|  | DGF-EX | 156 | 9, 9, 9 | 9 | 0 |
|  |  | 313 | 10, 8, 11 | 10 | 2 |
|  |  | 625 | 11, 11, 10 | 11 | 1 |
|  |  | 1,250 | 10, 8, 7 | 8 | 2 |
|  |  | 2,500 | 8*, 8*, 6* | 7 | 1 |
|  |  | 5,000 | 4*, 7*, 5* | 5 | 2 |
|  | 2-Aminoanthracene (2-AA) | 3.0 | 172, 170, 151 | 164 | 12 |
| TA1537 | Dimethylsulfoxide | 0 | 16, 11, 14 | 14 | 3 |
|  | DGF-EX | 39.1 | 15, 14, 19 | 16 | 3 |
|  |  | 78.1 | 14, 18, 14 | 15 | 2 |
|  |  | 156 | 18, 19, 15 | 17 | 2 |
|  |  | 313 | 20, 23, 19 | 21 | 2 |
|  |  | 625 | 10*, 13*, 12* | 12 | 2 |
|  |  | 1,250 | 11*, 8*, 4* | 8 | 4 |
|  | 2-Aminoanthracene (2-AA) | 3.0 | 235, 210, 214 | 220 | 13 |
| WP2uvrA(pKM101) | Dimethylsulfoxide | 0 | 161, 168, 177 | 169 | 8 |
|  | DGF-EX | 313 | 166, 172, 164 | 167 | 4 |
|  |  | 625 | 165, 149, 154 | 156 | 8 |
|  |  | 1,250 | 151, 160, 176 | 162 | 13 |
|  |  | 2,500 | 150, 163, 178 | 164 | 14 |
|  |  | 5,000 | 179, 153, 162 | 165 | 13 |
|  | 2-Aminoanthracene (2-AA) | 2.0 | 549, 543, 543 | 545 | 3 |

S.D: Standard Deviation
*indicates growth inhibition 3-2 Chromosome Aberration Assay In order to confirm genotoxicity of extract of flower of *Daphne genkwa*, a chromosome aberration assay was performed on the basis of the guidelines of Ministry of Food and Drug Safety in Biotoxtech, a GLP (Good Laboratory Practice) organization.

To confirm the structural aberration of the chromosome of DG-EX obtained in Example 1, the presence of structural aberration of the chromosome was evaluated using CHL (Chinese Hamster Lung)/IU cells, a mammalian cell line.

(1) Cell Proliferation Inhibition Test

For the highest capacity setting of this test, the chromosome aberration assay, cell proliferation inhibition test was carried out with the highest dose of DGF-EX 5,000 μg/mL at the following doses of 2,500, 1,250, 625, 313, 156, 78.1, 39.1, and 19.5 μg/ml.

As a result, cytotoxicity was observed in the presence or absence of the metabolic activation system and in the absence of the metabolic activation system of the continuous treatment method. The dose that specifically inhibited cell proliferation by more than 50% was more than 625 μg/mL in the presence and absence of the metabolic activation system of the short-term treatment method and more than 156 μg/mL in the absence of the metabolic activation system of the continuous treatment method. As a result of calculating the capacity to inhibit about 55% cell proliferation, 428.3 μg/mL in the absence of the metabolic activation system and 725 μg/mL in the presence of the metabolic activation system of the short-term treatment method, and 133.1 μg/mL in the absence of the metabolic activation system of the continuous treatment method.

Therefore, the capacity of this test was set as shown in Table 8 below. Also, a negative control and a positive control were set.

TABLE 8

| treatment | S9 mix | dose of the present test (μg/mL) |
|---|---|---|
| short-term treatment | – | 430, 215, 108, 53.8 |
|  | + | 730, 365, 183, 91.3 |
| continuous treatment | – | 140, 70.0, 35, 0, 17.5 |

(2) Chromosome Aberration Assay

As a result of the chromosome aberration assay, the frequency of cells with numerical aberration were less than 5% in the presence and absence of the metabolic activation system of the short-term treatment method and in the absence of the metabolism activity system of the continuous treatment method, and no chromosome aberration was observed, and no statistical significance was observed when compared with the negative control group. In the positive control group for each treatment group, the frequency of cells with aberrations was more than 10%, which was statistically significantly increased when compared to that in the negative control group. The results are shown in Table 9 below

TABLE 9

| Test substance | Dose (μg/mL) | RPD (%) | S9 mix | Trt-Rec Time (hr) | No. of cell analyzed | Number of cells with structural aberrations | | | | | | | | | Number of cells with numerical aberrations | | | |
|---|---|---|---|---|---|---|---|---|---|---|---|---|---|---|---|---|---|---|
| | | | | | | ctb | csb | cte | cse | frg | ctg | csg | gap | total (%) | | | total | Others[a)] |
| | | | | | | | | | | | | | gap– | gap+ | end | pol | (%) | |
| Dimethyl sulfoxide | 0 | 100 | – | 6-18 | 100 | 1 | 0 | 0 | 0 | 0 | 0 | 0 | 2(1.0) | 2(1.0) | 0 | 0 | 0(0.0) | 0 |
| | | | | | 100 | 1 | 0 | 0 | 0 | 0 | 0 | 0 | | | 0 | 0 | | |
| DGF-EX | 53.8 | 102 | – | 6-18 | 100 | | | | | | | | not observed | | | | | |
| | | | | | 100 | | | | | | | | | | | | | |
| | 108 | 102 | – | 6-18 | 100 | 0 | 0 | 0 | 0 | 0 | 0 | 0 | 0(0.0) | 0(0.0) | 0 | 0 | 0(0.0) | 0 |
| | | | | | 100 | 0 | 0 | 0 | 0 | 0 | 0 | 0 | | | 0 | 0 | | |
| | 215 | 97.6 | – | 6-18 | 100 | 0 | 0 | 1 | 0 | 0 | 0 | 0 | 1(0.5) | 1(0.5) | 0 | 1 | 1(0.5) | 0 |
| | | | | | 100 | 0 | 0 | 0 | 0 | 0 | 0 | 0 | | | 0 | 0 | | |
| | 430 | 75.0 | – | 6-18 | 100 | 0 | 0 | 1 | 0 | 0 | 0 | 0 | 1(0.5) | 1(0.5) | 0 | 3 | 5.(2.5) | 0 |
| | | | | | 100 | 0 | 0 | 0 | 0 | 0 | 0 | 0 | | | 0 | 2 | | |
| MMC | 0.1 | 80.4 | – | 6-18 | 100 | 5 | 0 | 18 | 0 | 0 | 0 | 0 | 38*(19.0) | 38(19.0) | 0 | 2 | 2(1.0) | 0 |
| | | | | | 100 | 4 | 0 | 14 | 0 | 0 | 0 | 0 | | | 0 | 0 | | |
| Dimethyl sulfoxide | 0 | 100 | + | 6-18 | 100 | 0 | 0 | 0 | 0 | 0 | 0 | 0 | 1(0.5) | 1(0.5) | 0 | 1 | 1(0.5) | 0 |
| | | | | | 100 | 1 | 0 | 0 | 0 | 0 | 0 | 0 | | | 0 | 0 | | |
| DGF-EX | 91.3 | 104 | + | 6-18 | 100 | | | | | | | | not observed | | | | | |
| | | | | | 100 | | | | | | | | | | | | | |
| | 183 | 98.4 | + | 6-18 | 100 | 0 | 0 | 0 | 0 | 0 | 0 | 0 | 0(0.0) | 0(0.0) | 0 | 0 | 0(0.0) | 0 |
| | | | | | 100 | 0 | 0 | 0 | 0 | 0 | 0 | 0 | | | 0 | 0 | | |
| | 365 | 77.4 | + | 6-18 | 100 | 1 | 0 | 0 | 0 | 0 | 0 | 0 | 2(1.0) | 2(1.0) | 1 | 1 | 2(1.0) | 0 |
| | | | | | 100 | 1 | 0 | 0 | 0 | 0 | 0 | 0 | | | 0 | 0 | | |
| | 730 | 53.4 | + | 6-18 | 100 | 0 | 0 | 2 | 0 | 0 | 0 | 0 | 2(1.0) | 2(1.0) | 0 | 3 | 5.(2.5) | 0 |
| | | | | | 100 | 0 | 0 | 0 | 0 | 0 | 0 | 0 | | | 0 | 2 | | |
| B[a]P | 20 | 57.4 | + | 6-18 | 100 | 5 | 0 | 15 | 0 | 0 | 0 | 0 | 31*(15.5) | 32(16.0) | 0 | 0 | 0(0.0) | 0 |
| | | | | | 100 | 2 | 0 | 13 | 0 | 0 | 1 | 0 | | | 0 | 0 | | |
| Dimethyl sulfoxide | 0 | 100 | – | 24-0 | 100 | 0 | 0 | 0 | 0 | 0 | 0 | 0 | 0(0.0) | 0(0.0) | 0 | 1 | 1(0.5) | 0 |
| | | | | | 100 | 0 | 0 | 0 | 0 | 0 | 0 | 0 | | | 0 | 0 | | |
| DGF-EX | 17.5 | 97.0 | – | 24-0 | 100 | | | | | | | | not observed | | | | | |
| | | | | | 100 | | | | | | | | | | | | | |
| | 35.0 | 94.4 | – | 24-0 | 100 | 2 | 0 | 0 | 0 | 0 | 0 | 0 | 2(1.0) | 2(1.0) | 0 | 1 | 1(0.5) | 0 |
| | | | | | 100 | 0 | 0 | 0 | 0 | 0 | 0 | 0 | | | 0 | 0 | | |
| | 70.0 | 93.5 | – | 24-0 | 100 | 0 | 0 | 0 | 0 | 0 | 0 | 0 | 1(0.5) | 1(0.5) | 0 | 1 | 1(0.5) | 0 |
| | | | | | 100 | 0 | 1 | 0 | 0 | 0 | 0 | 0 | | | 0 | 0 | | |
| | 140 | 57.1 | – | 24-0 | 100 | 0 | 0 | 0 | 0 | 0 | 0 | 0 | 1(0.5) | 1(0.5) | 0 | 1 | 1(0.5) | 0 |
| | | | | | 100 | 0 | 1 | 0 | 0 | 0 | 1 | 0 | | | 0 | 0 | | |

TABLE 9-continued

| | | | Trt-Rec | No. of | Number of cells with structural aberrations | | | | | | | | | Number of cells with numerical aberrations | | | |
|---|---|---|---|---|---|---|---|---|---|---|---|---|---|---|---|---|---|
| | | | | | | | | | | | | gap | total (%) | | | total | |
| Test substance | Dose (µg/mL) | RPD (%) | S9 mix | Time (hr) | cell analyzed | ctb | csb | cte | cse | frg | ctg | csg | gap− | gap+ | end | pol | (%) | Others[a] |
| MMC | 0.1 | 66.0 | − | 24-0 | 100 | 6 | 0 | 25 | 0 | 0 | 0 | 0 | 52*(26.0) | 52(26.0) | 0 | 0 | 0(0.0) | 0 |
| | | | | | 100 | 6 | 1 | 20 | 1 | 0 | 0 | 0 | | | 0 | 0 | | |

Abbreviation: ctg: chromatid gap, csg: chromosome gap, ctb: chromatid break, cte:chromatid exchange, csb: chromosome break, cse: chromosome exchange, frg: fragmentation, end: endoreduplication, pol: polyploidy, MMC: Mitomycin C, B[a]P: Benzo[a]pyrene, RPD: Relative Population Doubling, Trt-Rec time: Treatment-Recovery times, gap−: total number of cells with structural aberration except gap, gap+: total number of cells with structural aberration including gap
a): Excluded from the number of cells with chromosomal aberrations
*: p<0.01

From the above results, the chromosomal abnormality of the test substance DGF-EX was judged to be negative under this test condition.

Example 4

Confirming the Effect of the Extract of Flower of *Daphne genkwa* on the Nurr1 Activity To confirm the Nurr1 activation effect of DGF-EX obtained in Example 1, Nurr1 activity experiments were performed using the GAL4 assay system.

After a GAL4-LBD plasmid, a luciferase plasmid to which GAL4 can bind, and β-galactosidase were transfected into BE(2)C cells, which are neuroblasts of human origin, DGF-EX was treated for 16 hours at concentrations of 1, 25 and 40 ppm. The cells thus treated were cultured in a 5% carbon dioxide incubator at 37° C. for 20 hours, and the extract was dissolved in DMSO and treated. The control group was treated with 1% DMSO and then subjected to luciferase fluorescence analysis. The results are shown in FIG. 3.

Figure 3:
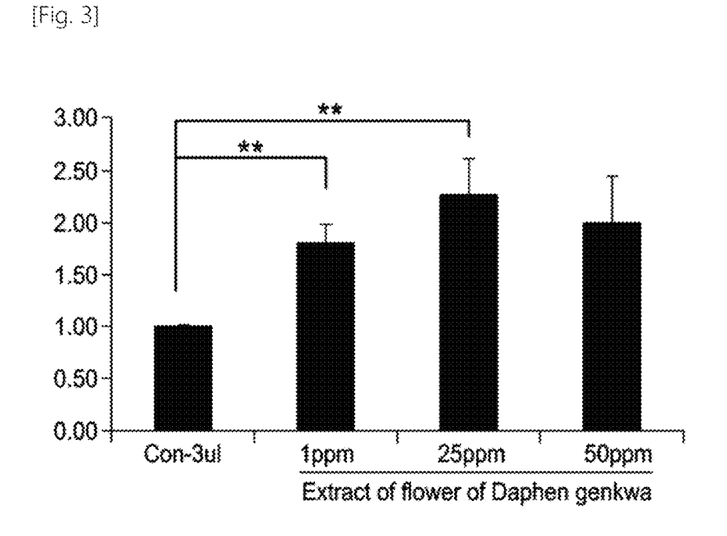
FIG. 3 is a graph showing the change in Nurr1 activity according to the concentration of extract of flower of *Daphne genkwa* through luciferase assay. Con-3ul means control group (1% DMSO). (**: $p<0.01$).

As shown in FIG. 3, it was confirmed that the activity of Nurr1 was increased by DGF-EX in BE(2)C cells. DGF-EX significantly activated Nurr1 at concentrations of 1 ppm and 25 ppm. In particular, DGF-EX showed maximum activity when treated at a concentration of 25 ppm, and exhibited Nurr1 activating activity about twice as much as the control.

Also, the Nurr1 activity of DGF-EX and DG-EX obtained in Comparative Example 1 was compared in the same manner as described above, and the results are shown in FIG. 4.

As shown in FIG. 4, DGF-EX showed 21, 23 and 120% higher activity at 1, 10 and 50 ppm than DG-EX, respectively.

Example 5

Identification of the Effect of the Extract of Flower of *Daphne genkwa* in Animal Model of Parkinson's Disease This study was carried out to investigate the effect of the extract of flower of *Daphne genkwa* in animal models of Parkinson's disease.

In order to specifically kill dopaminergic neurons in substantia nigra of midbrain, 6-OHDA(0.2 µg/µl, final volume 5 µl) was directly injected into the AP(−4.3), ML(−1.8), DV(−8.2), and AP(−5.0), ML(−1.8), DV(−8.2) regions of the brain using a stereotaxic tool in 18 6-week-old SD rats (Coatec.) to produce an animal model of Parkinson's disease as experimental group. Desipramine was administered at a dose of 25 mg/kg 30 minutes before the administration of 6-OHDA to inhibit cell death other than dopaminergic neurons. As a control group, 6 6-week-old SD rats (Coatec.) were injected with PBS instead of 6-OHDA.

Six of the 6-OHDA-lesioned 18 rats were vehicle treated (control group), and another 6 rats were fed a diet supplemented with 50 mg/kg of the daily dose of the extract of flower of *Daphne genkwa*, and the remaining 6 rats were fed a diet supplemented with 100 mg/kg of the daily dose of the extract of flower of *Daphne genkwa*.

A rotation test was performed at two and 4 weeks after surgery. When the dopamine receptor agonist, apomorphine is injected into an animal model of Parkinson's disease, a denervation supersensitivity of dopamine induces rotation to the opposite side of the lesion, which can be measured quantitatively using a rotometer. The results are shown in FIG. 5.

As shown in FIG. 5, it was confirmed that the extract of flower of *Daphne genkwa* was significantly reduced in the rats fed with the feed containing the rotomain of the apomorphine after two and 4 weeks even when administered at a low concentration in comparison with the usual administration concentrations of the extract of root of *Daphne genkwa*.

Example 6

Immunohistochemical Analysis of the Effect of the Extract of Flower of *Daphne genkwa* in Animal Model of Parkinson's Disease In Example 5, the therapeutic effect in the animal model of Parkinson's disease of the extract of flower of *Daphne genkwa* was confirmed, and we further investigated whether the death of dopaminergic neurons in the substantia nigra of midbrain was actually inhibited by the administration of the extract of flower of *Daphne genkwa*.

An animal model of Parkinson's disease was prepared in the same manner as in Example 5, and rats were sacrificed at 4 weeks after the surgery, and followed by perfusion with 4% paraformaldehyde. Brains were removed, and cut into a 40 µm coronal section using a vibratome and then subjected to immunostaining with a tyrosine hydroxylase antigen. The sections were treated with 3% hydrogen peroxide solution and washed 3 times with PBS. Then, after the sections were blocked with 5% horse serum for 1 hour at room temperature, tyrosine hydroxylase antigen was treated overnight at 4° C. The sections were washed with PBS and then treated with secondary antirabbit IgG and treated with avidin-biotinylated peroxidase complex and 3,3'-diaminobenzidine.

The color-developed and dyed dopaminergic neurons were observed under a microscope. The results are shown in FIG. 6, and the number of neurons was counted, and the results are shown in FIG. 7.

Figure 6:
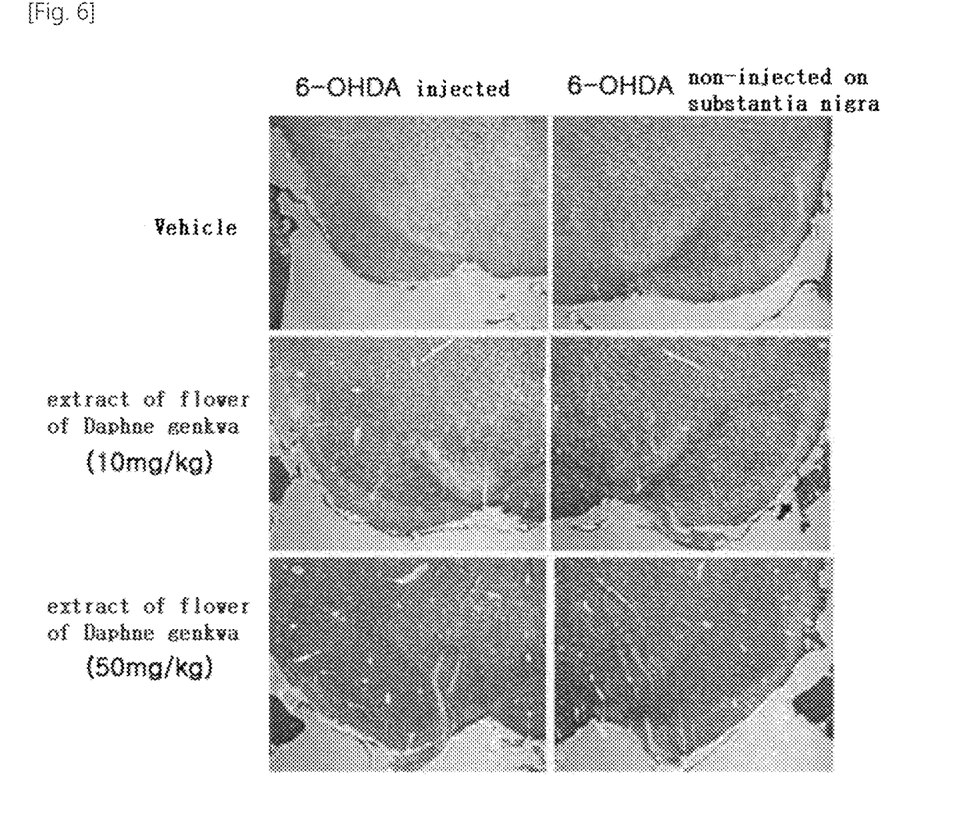
FIG. 6 shows immunohistochemical analysis of changes in dopaminergic neurons in the substantia nigra of midbrain after 4 weeks of feeding of the extract of flower of *Daphne genkwa* from 6-OHDA (6-hydroxydopamine) induced animal model of Parkinson's disease.

As shown in FIG. 6, when the left substantia nigra (6-OHDA) injected with 6-OHDA was compared with the right substantia nigra (unlesioned) not injected, for vehicle treated rats, the dopaminergic neurons in 6-OHDA-injected substantia nigra were significantly reduced when compared with normal substantia nigra. However, when 10 mg/kg and 50 mg/kg of the extract of flower of *Daphne genkwa* (DGF) were administered, the level of neurons similar to that of the normal substantia nigra was maintained even in the case of 6-OHDA-injected substantia nigra.

Figure 7:
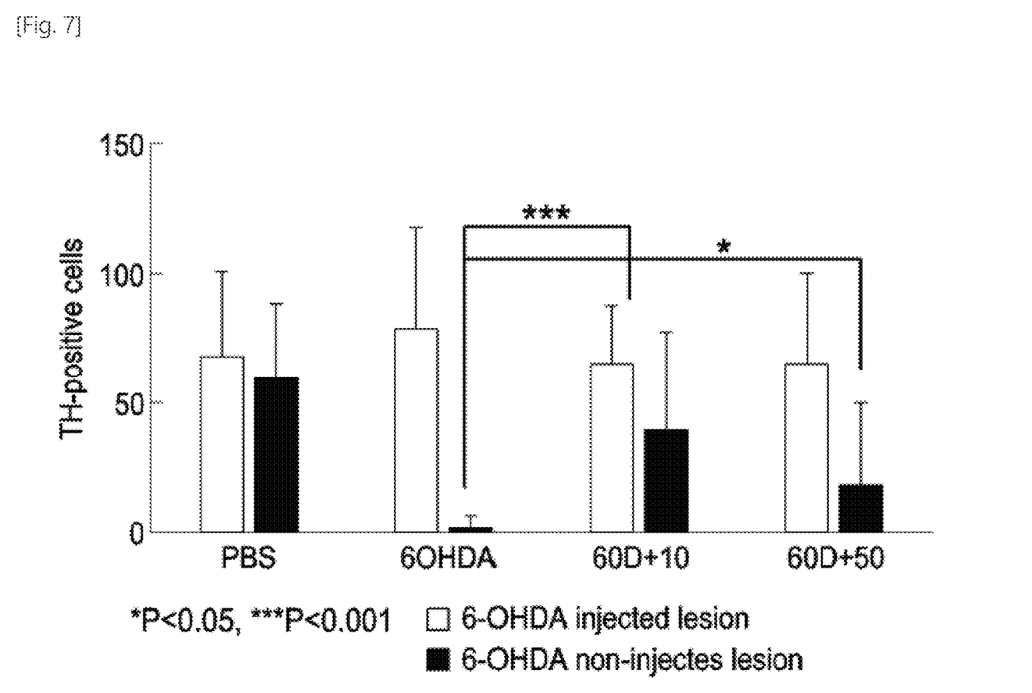
FIG. 7 is a graph comparing the number of dopaminergic neurons in the substantia nigra of midbrain after 4 weeks of feeding of the extract of flower of *Daphne genkwa* in 6-OHDA (6-hydroxydopamine) induced animal model of Parkinson's disease. PBS means a group not injected with 6-OHDA, 6-OHDA means a group injected in 6-OHDA, 6OD+10 means a group fed with 10 mg/kg of the extract of flower of *Daphne genkwa* after 6-OHDA injection, 6OD+50 means a group fed with 50 mg/kg of the extract of flower of *Daphne genkwa* after 6-OHDA injection.

Furthermore, as shown in FIG. 7, when 6-OHDA was injected, 97.5% of dopaminergic neurons were killed, but it was confirmed that the administration of 10 mg/kg and 50 mg/kg of the extract of flower of *Daphne genkwa* (DGF) significantly inhibited the death of dopaminergic neurons (39.6% and 70.1%, respectively)

This indicates that the extract of flower of *Daphne genkwa* (DGF) strongly inhibited dopaminergic neurons death by 6-OHDA.

What is claimed is:

1. A method of treating or ameliorating a neurodegenerative disease, comprising administering to a mammal in need thereof a composition comprising a therapeutically effective amount of an aqueous extract or lower-alkyl alcohol extract of flower or flower buds of *Daphne genkwa* or a fraction thereof, wherein the neurodegenerative disease is Parkinson's disease or frontotemporal dementia, and the therapeutically effective amount is 10 mg/kg to 100 mg/kg per day.

2. The method of claim 1, wherein the extract is a $C_1$ to $C_4$ alkyl alcohol extract.

3. The method of claim 1, wherein the extract is an ethanol extract.

4. The method of claim 1, wherein the extract comprises Genkwanin N or Yuanhuacine as an active ingredient.

5. The method of claim 1, wherein the composition is a pharmaceutical composition further comprising a pharmaceutically acceptable carrier.

6. The method of claim 1, wherein the composition is a health functional food composition comprising the extract as a food additive.

* * * * *